(12) United States Patent
Pollard-Knight et al.

(10) Patent No.: US 6,794,130 B2
(45) Date of Patent: Sep. 21, 2004

(54) ELECTRODE CAPTURE OF NUCLEIC ACID

(75) Inventors: Denise Vera Pollard-Knight, London (GB); Sophie Elizabeth Victoria Martin, Cambridge (GB); Susan Watson, Cambridge (GB)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 09/171,847

(22) PCT Filed: Apr. 25, 1997

(86) PCT No.: PCT/GB97/01148

§ 371 (c)(1),
(2), (4) Date: Mar. 11, 1999

(87) PCT Pub. No.: WO97/41219

PCT Pub. Date: Nov. 6, 1997

(65) Prior Publication Data

US 2001/0008762 A1 Jul. 19, 2001

(30) Foreign Application Priority Data

Apr. 26, 1996 (GB) .............................. 9608644

(51) Int. Cl.⁷ .......................... C12Q 1/68; G09B 11/06; G09B 19/00; G09B 27/08; G09B 9/00
(52) U.S. Cl. .............................. 435/6; 422/88; 422/99; 422/101; 422/122; 422/131; 422/50; 422/61; 422/73; 422/71; 422/186
(58) Field of Search ...................... 435/6, 91.2; 422/88, 422/99, 101, 173, 71, 186, 122, 131, 61, 50; 536/25.4

(56) References Cited

U.S. PATENT DOCUMENTS 4,965,188 A * 10/1990 Mullis et al. .................. 435/6
5,155,361 A   10/1992 Lindsay ....................... 250/307
5,527,670 A * 6/1996 Stanley .......................... 435/6
5,776,672 A * 7/1998 Hashimoto et al. ............. 435/6

FOREIGN PATENT DOCUMENTS

| WO | WO92/04470 | 3/1992 | ............ C12Q/1/68 |
| WO | WO95/34569 | 12/1995 | ............ C07H/1/08 |
| WO | WO96/07917 | 3/1996 | .......... G01N/35/00 |

OTHER PUBLICATIONS

Teijeiro et al., Cyclic voltammetry of submicrogram quantities of supercoiled, linear and denatued DNAs with DNA–modified mercury electrode, J. of biomolecular structure and dynamics, vol. 11(2), p. 313–331, 1993.*
Harrington et al. DNA transformation using electrically charged tungsten microelectrodes, IEEE, p. 12–16, 1995.*
S. M. Lindsay et al., "Potentiostatic Deposition of DNA for Scanning Probe Microscopy," Biophysical Journal, vol. 61, Jun. 1992, pp. 1570–1584.
E. Palacek, "Adsorptive Transfer Stripping Voltammetry Determination of Nanogram Quantities of DNA Immobilized at the Electrode Surface," Analytical Biochemistry, vol. 170, No. 2, (1988) pp. 421–431.
Palecek, E., "New Trends in Electrochemical Analysis of Nucleic Acids," *Bioelectrochemistry and Bioenergetics* 20:179–194 (1988).

* cited by examiner

*Primary Examiner*—Kenneth R. Horlick
*Assistant Examiner*—Joyce Tung
(74) *Attorney, Agent, or Firm*—Morgan, Lewis & Bockius LLP

(57) ABSTRACT

Nucleic acid is captured from a mixture of cellular debris produced by cell lysis by exposing the mixture to an electrode and applying a nucleic acid capturing voltage to the electrode which is then removed from the mixture carrying said nucleic acid. The nucleic acid is undamaged and can be amplified by PCR.

22 Claims, 2 Drawing Sheets

M: marker; M2: 500bp marker; +C: PCR control; OV: with electrode, no current; 0.5-8V.

| | |
|---|---|
| M | 410bp marker thermally amplified from pBR322 |
| C | PCR carried out on cell slurry using primers for 410bp from pBR322 |
| OC | 0 voltage applied |
| 1 | 1 volt applied |
| 2 | 2 volts applied |
| 4 | 4 volts applied |

ELECTRODE CAPTURE OF NUCLEIC ACID

The present invention relates to processes for the manipulation of nucleic acids and in particular for capturing a nucleic acid or mixture of nucleic acids from cellular debris or other biomolecule mixtures.

When cells are lysed to release nucleic acids, the resulting mixture is complex. It may contain cell wall materials, proteins, polysaccharides and numerous other materials. To capture the nucleic acids contained therein has been a time consuming task which generally must be carried out before the nucleic acid can be used in other processes such as replication (or amplification) procedures or hybridisation assays.

Harrington et al in "DNA transformation with electrically charged tungsten microelectrodes", International Worm Meeting, abstract 240 disclosed that a tungsten microelectrode subjected to a voltage of 3 V would attract DNA from solution to enable the DNA to be introduced into nematode worms. The DNA remained on the electrode when the latter was withdrawn from the solution. Reversal of the voltage is mentioned as a method of displacing the DNA from the electrode, although this is not disclosed to be advantageous. The DNA was present in pure form in a suitable buffer.

We have now discovered that a similar method can be employed to remove DNA or other nucleic acids from the complex mixtures formed during cell lysis, i.e. from admixture with cellular debris or form mixtures with other biomolecules generally, and that the nucleic acids so obtained can be removed from the electrode without damage so that they may be used in subsequent processes. Accordingly, the present invention now provides a method for capturing nucleic acid from a mixture of said nucleic acid with other biomolecules, e.g. cellular debris, comprising exposing an electrode to said mixture and applying to said electrode a nucleic acid attracting voltage, and removing said electrode from said mixture carrying said nucleic acid thereon.

The electrode may be removed from the mixture by physical movement of the electrode or by removal of the mixture, e.g. by washing.

A voltage of from 0 to 4, more preferably 0.5 to 3 volts is suitably applied to said electrode to attract said nucleic acid thereto. Generally, best results are obtained at approximately 1 V. Said electrode carrying said nucleic acid may then be exposed to a liquid into which said nucleic acid is to be introduced and said nucleic acid may be removed from said electrode into said liquid. This may be achieved by washing, preferably after reducing, turning off or reversing the electrical field. The voltage may be applied between a pair of electrodes which are both removed from the mixture, or only one electrode carrying said nucleic acid may be removed.

The removed nucleic acid may then be used as desired, e.g. subjected to a replication procedure or a hybridisation assay.

The mixture from which the nucleic acid is removed may be produced by a process of cell lysis as described in our PCT application PCT/GB95/02024. As described there, cells such as bacteria (e.g. E. Coli) may be lysed by subjecting them to a voltage of a few volts, e.g. 1 to 10 volts. Using the same electrode, the released nucleic acid may be captured and removed as described above. This provides a particularly elegant process for lysing cells and capturing nucleic acids from thecells.

Other crude mixtures from which to purify nucleic acids, especially DNA, include PCR or other amplification reaction mixes, sequencing reaction mixes, body fluid samples, e.g. blood or sputum or other DNA rich samples, e.g. micro-biological cultures.

For conducting processes such as nucleic acid amplification or hybridisation assays, it is generally necessary to denature DNA into single stranded form. As disclosed in WO92/04470, WO93/15224 and PCT/GB9500542, this also may be achieved by applying a voltage to an electrode. Such methods of denaturation may be used in the further treatment of DNA captured by the methods described herein.

In the accompanying drawings.

The present invention will be illustrated by the following examples.

EXAMPLE 1

To illustrate the principle of the invention, DNA was captured from solution, transferred to a separate container and amplified by PCR to demonstrate the integrity of the DNA so captured.

A variety of voltages were applied to 1 $\mu$g ml$^{-1}$ of a 500 base pair lambda DNA in 1×PCR buffer solution using a pair of blunt ended carbon electrodes. Captured DNA was removed from the solution on one of the electrodes and transferred to distilled water where reversal of the applied voltage was employed to displace the DNA into the water.

Figure 1:
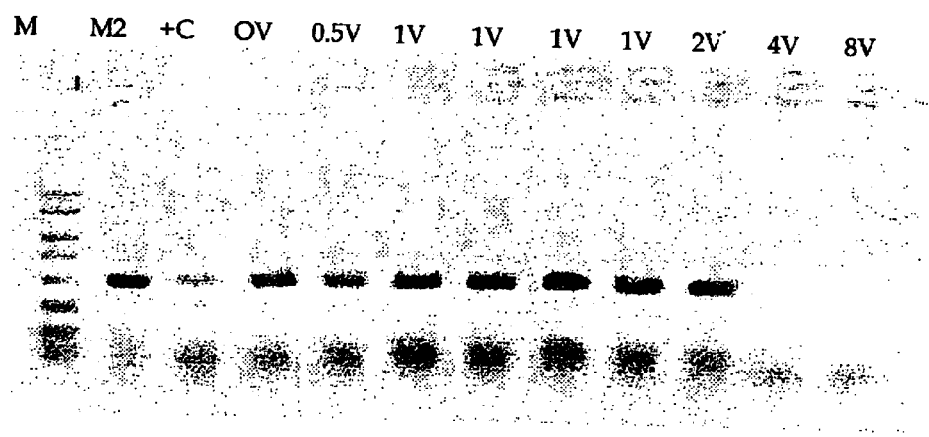
FIG. 1 is a gel produced in Example 1 as described below.

The transferred DNA was subjected to a conventional PCR procedure using the 500 bp fragment as template under the following FCR conditions:

60.5 $\mu$l transferred DNA in water 0.8 $\mu$M reverse primer 0.8 $\mu$M forward primer 2.5 U Taq polymerase 200 $\mu$M dNTP mix buffer—10 mM Tris.Cl (pH 8.3 at 25° C.), 50 mM KCl, 0.1% gelatin 2.5 mM MgCl$_2$ water to 100 $\mu$l The resulting amplicons were run on a gel and the results are shown in FIG. 1. The strongest amplification bands were achieved by adsorbing the template DNA onto the electrode at a voltage of +1 V. No amplification was seen when the DNA had been adsorbed at voltages of 4 or 8 V.

EXAMPLE 2

The aim here was to capture transformed pBR322, released from lysed E. coli cells, on to an electrode surface and to confirm this by thermal amplification of a 410 bp fragment of the plasmid.

E. coli cells containing pBR322 were grown up overnight at 37° C. in LB broth containing 25 $\mu$g/ml ampicillin.

The cells (approximately 1×10$^9$ cfu/ml) were harvested by spinning down 100 ml of culture, resuspending in 40 mls, 10 mM Tris pH8.0 and further concentrating the cells into 10 mls 1×PCR buffer. The stock culture was lysed by heating for 5 mins at 98° C. and held on ice until use.

Voltages of between 0 and 4 volts were applied to 59.5 $\mu$l of the culture for 30 seconds using blunt ended carbon electrodes. Following the application of the field the electrodes were removed and placed into an equal volume HPLC grade water and the field reversed for 30 seconds to displace the DNA.

The water containing the displaced DNA was then used in a conventional thermal PCR reaction using the pBR322 plasmid as the template under the following conditions:

59.5 µl HPLC grade water containing the displaced DNA
0.4 µM forward primer
0.4 µM reverse primer
10 mM Tris. Cl(pH8.3 at 25° C.), 50 mM KCl, 0.01% (W/v) gelatin
2.5 mM $MgCl_2$
200 µM of each dNTP Two control experiments were carried out, one where the described procedure was carried out in the absence of the field to demonstrate the background following passive binding. The second was a thermal PCR carried out on the cell slurry, where 5 µl was used in a 50 µl reaction.

Thermal amplification was carried out for 20 cycles.

The resulting amplicons were run on a 1% ethidium bromide stained agarose gel.

Figure 2:
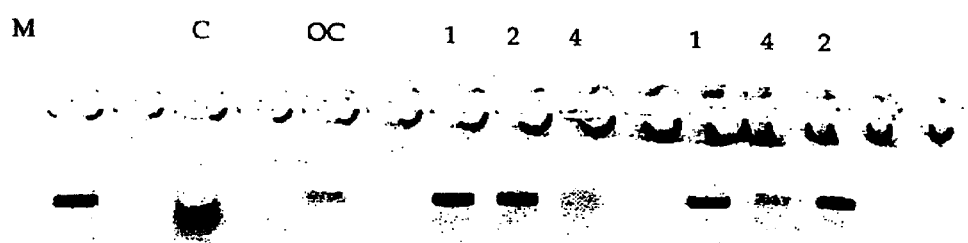
FIG. 2 is a gel produced in Example 2 as described below.

Amplification is seen in FIG. 2 following adsorption of the template on to the electrode at +1 and +2 volts. There is a smeared band present following adsorption of the DNA using +4 volts indicating degradation of the plasmid. Amplification is seen in the absence of the field but it is considerably lower than those where the voltage had been applied. No specific amplicon is observed where crude cell slurry was used as template, indicating that the presence of debris is inhibiting the reaction. This illustrates that the invention is also a method of purification as the plasmid (target) DNA has been preferentially removed from the slurry to give a clean and specific amplicon.

Many modifications and variations of the invention as described above may be made in accordance with the invention. For instance by using larger scale apparatus, particularly larger area electrodes, larger quantities of nucleic acid could be purified, enabling detection by less sensitive techniques than PCR. The techniques described herein may be used for concentrating nucleic acids by extracting them from a larger volume of liquid and releasing them into a smaller volume.

What is claimed is:

1. A method for purifying nucleic acid from a mixture of nucleic acid and non-nucleic acid biomolecules, comprising:
   (a) exposing an electrode to a mixture comprising said nucleic acid and non-nucleic acid biomolecules,
   (b) applying to said electrode a nucleic acid attracting voltage to capture said nucleic acid directly thereon,
   (c) removing said electrode carrying said nucleic acid directly thereon from said mixture to preferentially remove said nucleic acid from said non-nucleic acid biomolecules in said mixture,
   (d) recovering nucleic acid captured in step (b) from said electrode by exposing said electrode carrying said nucleic acid directly thereon to a liquid into which said nucleic acid is to be introduced, and
   (e) releasing said nucleic acid from said electrode into said liquid.

2. A method as claimed in claim 1, wherein said nucleic aid is DNA.

3. A method for purifying nucleic acid from a mixture of nucleic acid and non-nucleic acid biomolecules, comprising:
   (a) exposing an electrode to a mixture comprising said nucleic acid and non-nucleic acid biomolecules,
   (b) applying to said electrode a nucleic acid attracting voltage to capture said nucleic acid directly thereon,
   (c) removing said electrode carrying said nucleic acid directly thereon from said mixture to preferentially remove said nucleic acid from said non-nucleic acid biomolecules in said mixture,
   (d) recovering nucleic acid captured in step (b) from said electrode by exposing said electrode carrying said nucleic acid directly thereon to a liquid into which said nucleic acid is to be introduced, and
   (e) releasing said nucleic acid from said electrode into said liquid, wherein said liquid into which said nucleic acid is released is distilled water.

4. A method as claimed in claim 1, wherein the removed nucleic acid is subjected to a replication procedure.

5. A method as claimed in claim 1, wherein the removed nucleic acid is subjected to a hybridization assay procedure.

6. A method for purifying nucleic acid from a mixture of nucleic acid and cellular debris, comprising:
   (a) exposing an electrode to said mixture and applying to said electrode a nucleic acid attracting voltage so as to capture said nucleic acid directly on said electrode and thereby separate the nucleic acid from said cellular debris,
   (b) removing said electrode from said mixture carrying said nucleic acid directly thereon, and
   (c) separating the nucleic acid captured in step (a) from said electrode.

7. A method as claimed in claim 6, wherein said nucleic acid is DNA.

8. A method as claimed in claim 6, wherein said cellular debris is at least one material selected from the group consisting of cell wall materials, proteins, and polysaccharides.

9. A method for purifying nucleic acid from a mixture of nucleic acid and cellular debris, comprising:
   (a) exposing an electrode to said mixture and applying to said electrode a nucleic acid attracting voltage,
   (b) removing said electrode from said mixture carxying said nucleic acid directly thereon,
   (c) separating the nucleic acid captured in step (a) from said electrode, wherein said electrode carrying said nucleic acid is exposed to a liquid into which said nucleic acid is to be introduced and said nucleic acid is removed from said electrode into said liquid, said liquid being distilled water.

10. A method as claimed in claim 6, wherein said removed nucleic acid is subjected to replication.

11. A method as claimed in claim 6, wherein said removed nucleic acid is subject to amplification.

12. A method as claimed in claim 6, wherein said removed nucleic acid is subjected to hybridization.

13. A method for preferentially removing a nucleic acid from a mixture, comprising:
   (a) providing a mixture in which nucleic acids have been released;
   (b) exposing an electrode to said mixture, wherein a voltage is applied to said electrode to capture said nucleic acid directly thereon and separate the same from the rest of said mixture;
   (c) removing said electrode on which said nucleic acid is captured directly thereon from other non-nucleic acid materials in said mixture; and
   (d) subsequently removing said captured nucleic acid from said electrode.

14. A method as claimed in claim 13, further comprising lysing a cell to release said nucleic acids.

15. A method as claimed in claim 13, wherein said mixture further comprises cell wall materials, proteins, or polysaccharides.

16. A method for preferentially removing a nucleic acid from a mixture, comprising:
(a) providing a mixture in which nucleic acids have been released;
(b) exposing an electrode to said mixture, wherein a voltage is applied to said electrode to capture said nucleic acid directly thereon;
(c) removing said electrode on which said nucleic acid is captured directly thereon from other non-nucleic acid materials in said mixture; and
(d) subsequently removing said captured nucleic acid from said electrode and replicating, amplifying, or hybridizing said preferentially removed nucleic acid, wherein a voltage of from 0.5 to 3 volts is applied to said electrode to capture said nucleic acid directly thereon.

17. A method as claimed in claim 13, wherein said preferentially removed nucleic acid is replicated or amplified.

18. A method as claimed in claim 13, wherein said preferentially removed nucleic acid is hybridized.

19. A method as claimed in claim 1 wherein the liquid into which said nucleic acid is released is water.

20. A method as claimed in claim 6 wherein said electrode carrying said nucleic acid is exposed to water to remove the nucleic acid therefrom.

21. A method for purifying nucleic acid from a mixture of nucleic acid and non-nucleic acid biomolecules, comprising:
(a) exposing an electrode to a mixture comprising said nucleic acid and non-nucleic acid biomolecules,
(b) applying to said electrode a nucleic acid attracting voltage to capture said nucleic acid directly thereon,
(c) removing said electrode carrying said nucleic acid directly thereon from said mixture to preferentially remove said nucleic acid from said non-nucleic acid biomolecules in said mixture,
(d) recovering said nucleic acid from said electrode by exposing said electrode carrying said nucleic acid thereon to a liquid into which said nucleic acid is to be introduced and releasing the nucleic acid captured in step (b) from said electrode into said liquid, wherein a voltage of from about 0.5 to about 3 volts is applied to said electrode to attract said nucleic acid thereto.

22. A method for purifying nucleic acid from a mixture of nucleic acid and cellular debris, comprising:
(a) exposing an electrode to said mixture,
(b) applying to said electrode a nucleic acid attracting voltage,
(c) removing said electrode from said mixture carrying said nucleic acid directly thereon, and
(d) separating the nucleic acid captured in step (b) from said electrode, wherein a voltage of from about 0.5 to about 3 volts is applied to said electrode to attract said nucleic acid thereto.

* * * * *